(12) United States Patent
Cheng et al.

(10) Patent No.: US 12,004,720 B2
(45) Date of Patent: Jun. 11, 2024

(54) PACKAGED IMAGE SENSOR AND ENDOSCOPE

(71) Applicant: Medimaging Integrated Solution, Inc., Hsinchu (TW)

(72) Inventors: Chu-Ming Cheng, Hsinchu (TW); Shangyi Wu, Hsinchu (TW); Chia-Jung Lee, Hsinchu (TW); Chih-Lu Hsu, Hsinchu (TW)

(73) Assignee: MEDIMAGING INTEGRATED SOLUTION, INC., Hsinchu (TW)

( * ) Notice: Subject to any disclaimer, the term of this patent is extended or adjusted under 35 U.S.C. 154(b) by 0 days.

(21) Appl. No.: 17/476,808

(22) Filed: Sep. 16, 2021

(65) Prior Publication Data

US 2022/0265132 A1    Aug. 25, 2022

(30) Foreign Application Priority Data

Feb. 19, 2021   (TW) .................................. 110105869

(51) Int. Cl.
| | | |
|---|---|---|
| *A61B 1/05* | (2006.01) | |
| *A61B 1/00* | (2006.01) | |
| *A61B 1/005* | (2006.01) | |
| *A61B 1/06* | (2006.01) | |
| *H01L 27/146* | (2006.01) | |

(Continued)

(52) U.S. Cl.
CPC ............ *A61B 1/051* (2013.01); *A61B 1/0011* (2013.01); *A61B 1/00124* (2013.01); *A61B 1/0057* (2013.01); *A61B 1/0676* (2013.01); *H01L 27/14618* (2013.01); *H01L 31/0203* (2013.01); *H01L 31/02325* (2013.01); *H01L 31/173* (2013.01); *A61B 1/018* (2013.01)

(58) Field of Classification Search
CPC ... A61B 1/051; A61B 1/0011; A61B 1/00124; A61B 1/0057; A61B 1/0676; A61B 1/018; A61B 1/00114; A61B 1/00195; A61B 1/0684; H01L 27/14618; H01L 31/0203; H01L 31/02325; H01L 31/173; H01L 25/167; H01L 25/165; H04N 5/2253; H04N 5/2256; H04N 2005/2255; H05K 1/117; H05K 2201/10287

See application file for complete search history.

(56) References Cited

U.S. PATENT DOCUMENTS

| | | | | |
|---|---|---|---|---|
| 8,317,104 B2 * | 11/2012 | Havens | ............. | H01L 27/14618 235/454 |
| 9,748,293 B1 * | 8/2017 | Li | .......................... | H04N 23/57 |

(Continued)

*Primary Examiner* — Howard D Brown, Jr.
(74) *Attorney, Agent, or Firm* — MUNCY, GEISSLER, OLDS & LOWE, P.C.

(57) ABSTRACT

A packaged image sensor includes a substrate, an image sensor, a light-emitting element, and a first encapsulant. The substrate includes a through-hole. The image sensor and the light-emitting element are disposed on the substrate and are electrically connected to the substrate. The first encapsulant is filled between the image sensor and the light emitting element, and keeps the through-hole of the substrate opened. The through-hole of the substrate of the above-mentioned packaged image sensor can define a relative position between a pipe and the image sensor to facilitate the subsequent packaging process. An endoscope including the above-mentioned packaged image sensor is also disclosed.

12 Claims, 6 Drawing Sheets

(51) Int. Cl.
  *H01L 31/0203* (2014.01)
  *H01L 31/0232* (2014.01)
  *H01L 31/173* (2006.01)
  *A61B 1/018* (2006.01)

(56) References Cited

U.S. PATENT DOCUMENTS

| | | | |
|---|---|---|---|
| 10,121,820 B1* | 11/2018 | Chen | H01L 27/14685 |
| 10,561,306 B2* | 2/2020 | Ohno | A61B 1/051 |
| 2008/0255416 A1* | 10/2008 | Gilboa | A61B 1/055 |
| | | | 600/110 |
| 2010/0200898 A1* | 8/2010 | Lin | H01L 31/0203 |
| | | | 257/E31.11 |
| 2016/0163681 A1* | 6/2016 | Lee | H01L 31/02327 |
| | | | 257/432 |
| 2018/0042460 A1* | 2/2018 | Wake | A61B 1/00119 |
| 2018/0081163 A1* | 3/2018 | Lin | A61B 1/0676 |
| 2022/0265130 A1* | 8/2022 | Wu | G02B 23/2415 |
| 2023/0284885 A1* | 9/2023 | Huang | A61B 1/0057 |

\* cited by examiner

PACKAGED IMAGE SENSOR AND ENDOSCOPE

BACKGROUND OF THE INVENTION

1. Field of the Invention

The present invention relates to a packaged image sensor and an endoscope, particularly to a packaged image sensor including a working channel and an endoscope using the same.

2. Description of the Prior Art

Endoscopes can reach the cavities of an object, which the naked eyes are unlikely to observe directly, and capture images therefrom. Therefore, endoscopes have been extensively used in industry and medicine. The application of endoscopes particularly has significant influence in medicine. Endoscopes are required to access target cavities of human bodies through various small channels. For an example, a bronchoscope accesses the lung through a bronchial. For another example, a cystoscope accesses the bladder through the urethra. Hence, miniaturizing an endoscope is an important subject of the concerned field.

Figure 1:
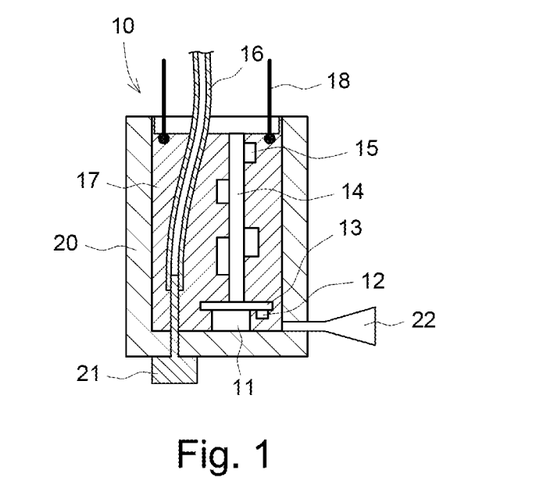
FIG. 1 and FIG. 2 are diagrams schematically showing a conventional image sensor module of an endoscope.
Figure 2:
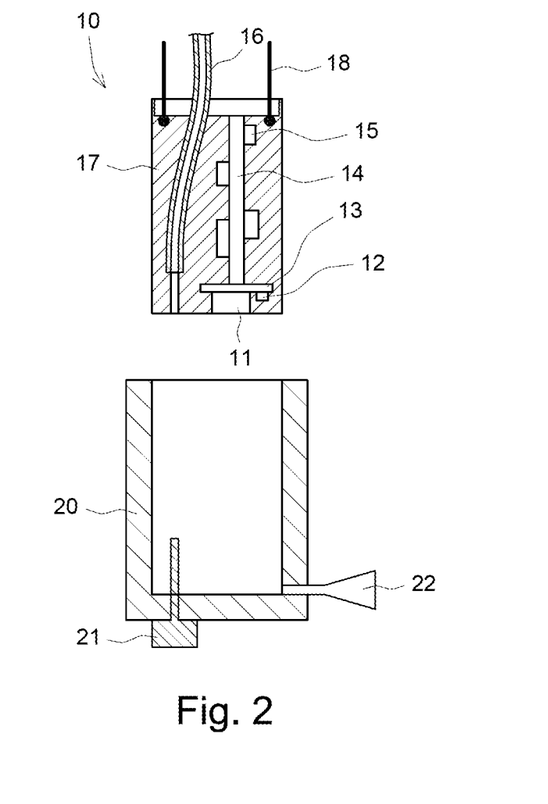

Refer to FIG. 1 and FIG. 2. In an image sensing module 10 of a conventional endoscope, an image sensing element 11 and a light-emitting element 12 are disposed on a substrate 13. The other side of the substrate 13 is connected with a circuit board 14. The circuit board 14 has electronic elements 15. The abovementioned elements are placed inside a mold 20. A pipe 16 functioning as a working channel sleeves a protrudent element 21 inside the mold 20, whereby to fix the relative position of the pipe 16 and the image sensing element 11. Next, an encapsulant 17 is filled into the mold 20 through a filling hole 22. After the encapsulant 17 is cured, demolding is undertaken to obtain the image sensing module 10.

As shown in FIG. 1 and FIG. 2, the pipe 16 tightly sleeves the protrudent element 21, and the aspect ratio of the mold 20 is relatively larger, which will lead to difficulty of demolding. Besides, a plurality of steering control wires 18, which are used to steer the image sensing module 10, are connected to the proximal end of the image sensing module 10. In other words, the steering control wires 18 are far away from the top end of the image sensing module 10. Thus, the image sensing module 10 has a larger bending radius, which will inconvenience operation. For example, the distance between the top end of the image sensing module 10 and the connection position of the steering control wires 18 is about 10 to 12 mm.

Accordingly, the manufacturers are eager to develop an endoscope that is easy to fabricate.

SUMMARY OF THE INVENTION

The present invention provides a packaged image sensor and an endoscope using the same, wherein an image sensor and a light-emitting element are disposed on a substrate. The substrate includes a through-hole. In the packaging process, the relative position of a pipe and the image sensor can be fixed as long as the pipe is disposed inside the through-hole of the substrate. Further, after an encapsulant is cured inside a mold chase, demolding is easy to be performed in the present invention.

In one embodiment, the packaged image sensor of the present invention comprises a substrate, an image sensor, a light-emitting element, and a first encapsulant. The substrate includes a plurality of first electric-conduction contacts, a plurality of second electric-conduction contacts, and a plurality of third electric-conduction contacts, wherein the plurality of second electric-conduction contacts and the plurality of third electric-conduction contacts are electrically connected with the plurality of corresponding first electric-conduction contacts. The substrate also includes a through-hole. The image sensor is disposed on the substrate and electrically connected with the plurality of second electric-conduction contacts. The light-emitting element is disposed on the substrate and near the image sensor. The light-emitting element is electrically connected with the plurality of third electric-conduction contacts. The first encapsulant is filled into the space between the image sensor and the light-emitting element with the through-hole of the substrate kept opened.

In one embodiment, the endoscope of the present invention comprises a tube, a packaged image sensor and an electric connector. The tube includes a first opening and a second opening, wherein the end of the first opening of the tube is used to extend to a cavity. The packaged image sensor is disposed at the first opening end of the tube, used to capture images of the cavity of the human body and generating corresponding electronic signals. The packaged image sensor includes a substrate, an image sensor, a light-emitting element, a first encapsulant, a pipe, a plurality of conductive wires and a second encapsulant. The substrate includes a plurality of first electric-conduction contacts, a plurality of second electric-conduction contacts, and a plurality of third electric-conduction contacts, wherein the plurality of second electric-conduction contacts and the plurality of third electric-conduction contacts are electrically connected with the plurality of corresponding electric-conduction contacts corresponding to them. The substrate also includes a through-hole. The image sensor is disposed on the substrate and electrically connected with the plurality of second electric-conduction contacts. The light-emitting element is disposed on the substrate and near the image sensor. The light-emitting element is electrically connected with the plurality of third electric-conduction contacts. The first encapsulant is filled into the space between the image sensor and the light-emitting element and keep the through-hole of the substrate opened. The pipe is disposed inside the through-ole and protrudes from the surface of the substrate where the first electric-conduction contacts are disposed. The plurality of conductive wires are disposed inside the tube, and one end of the plurality of conductive wires is electrically connected with the plurality of corresponding first electric-conduction contacts of the substrate. The second encapsulant encapsulates the light-emitting element, a circuit, one end of a plurality of conductive wires and a portion of the pipe with two ends of the pipe kept opened. The electric connector is electrically connected with the other ends of the plurality of conductive wires, whereby the endoscope may be electrically with an external electronic device in a pluggable way.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily

DESCRIPTION OF THE PREFERRED EMBODIMENTS

Various embodiments of the present invention will be described in detail below and illustrated in conjunction with the accompanying drawings. In addition to these detailed descriptions, the present invention can be widely implemented in other embodiments, and apparent alternations, modifications and equivalent changes of any mentioned embodiments are all included within the scope of the present invention and based on the scope of the Claims. In the descriptions of the specification, in order to make readers have a more complete understanding about the present invention, many specific details are provided; however, the present invention may be implemented without parts of or all the specific details. In addition, the well-known steps or elements are not described in detail, in order to avoid unnecessary limitations to the present invention. Same or similar elements in Figures will be indicated by same or similar reference numbers. It is noted that the Figures are schematic and may not represent the actual size or number of the elements. For clearness of the Figures, some details may not be fully depicted.

Figure 3:
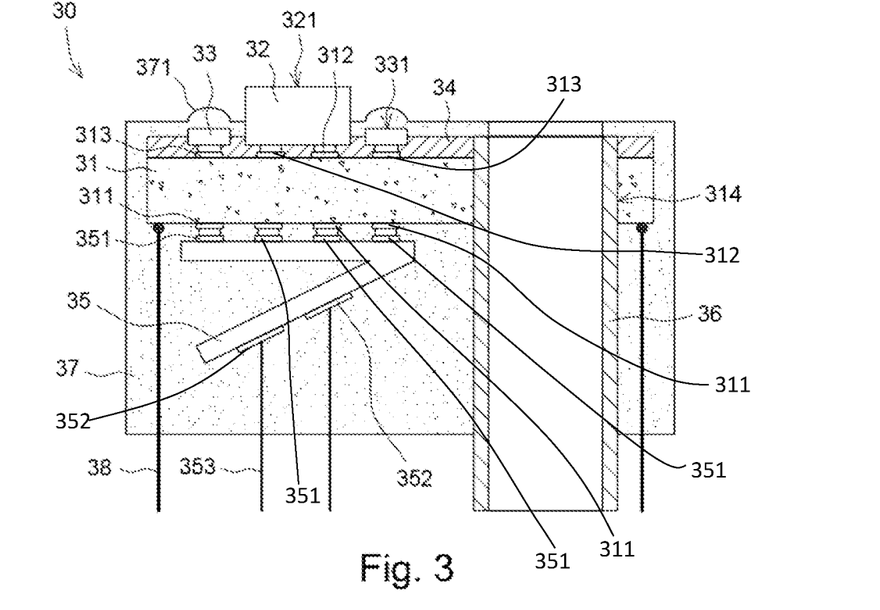
FIG. 3 is a diagram schematically showing a packaged image sensor according to a first embodiment of the present invention.

Refer to FIG. 3. In one embodiment, the packaged image sensor 30 of the present invention comprises a substrate 31, an image sensor 32, a light-emitting element 33, and a first encapsulant 34. The substrate 31 includes a plurality of first electric-conduction contacts 311, a plurality of second electric-conduction contacts 312, and a plurality of third electric-conduction contacts 313, wherein the plurality of second electric-conduction contacts 312 and the plurality of third electric-conduction contacts 313 are electrically connected with the plurality of corresponding first electric-conduction contacts 311. In one embodiment, the plurality of second electric-conduction contacts 312 and the plurality of third electric-conduction contacts 313 are disposed on one side opposite to the plurality of first electric-conduction contacts 311. Besides, the substrate 31 also includes a through-hole 314. In one embodiment, the substrate 31 is a ceramic substrate.

The image sensor 32 is disposed on the substrate 31 and electrically connected with the corresponding second electric-conduction contacts 322. The light-emitting element 33 is disposed on the substrate 31 and near the image sensor 32. The light-emitting element 33 is electrically connected with the corresponding third electric-conduction contacts 313. In one embodiment, the packaged image sensor 30 comprises a plurality of light-emitting elements 33. The plurality of light-emitting elements 33 may respectively emit light beams having different wavelengths or spectrums. The plurality of light-emitting elements 33 may be simultaneously or separately operated for observations of different targets. It is easily understood: the plurality of light-emitting elements 33 may emit light beams having the same wavelength for illumination or another target. For example, the light-emitting elements 33 may be white light-emitting diodes (LED), infrared LEDs, blue LED, ultraviolet LEDs, or a combination thereof.

The first encapsulant 34 is filled into the space between the image sensor 32 and the light-emitting element 33. It is easily understood: the first encapsulant 34 is not allowed to cover or overflow to the through-hole 314 of the substrate 31. In other words, the through-hole 314 is kept opened. In one embodiment, the first encapsulant 34 is made of a semi-transparent or opaque resin, whereby to prevent the imaging system of the image sensor 32 from being influenced by the illumination light or stray light, which is emitted by the light-emitting element 33. For example, the semi-transparent resin may have a transmittance of 0.01 to 50%. It is easily understood: the light-output surface 331 of the light-emitting element 33 must be higher than the top surface of the first encapsulant 34 lest the light output of the light-emitting element 33 be influenced. In other words, the first encapsulant 34 cannot cover the light-output surface 331 of the light-emitting element 33.

In one embodiment, the packaged image sensor 30 further comprises a circuit board 35 and a plurality of conductive wires 353. The circuit board 35 includes a plurality of fourth electric-conduction contacts 351 and a plurality of fifth electric-conduction contacts 352. The plurality of fourth electric-conduction contacts 351 is electrically connected with the plurality of corresponding first electric-conduction contacts 311 of the substrate 31. In one embodiment, the circuit board 35 may be a printed circuit board (PCB) or a flexible printed circuit (FPC). The plurality of conductive wires 353 is electrically connected with the plurality of corresponding fifth electric-conduction contacts 352. The plurality of conductive wires 353 may act as power wires and signal transmission wires, whereby the packaged image sensor 30 may be electrically connected with the exterior. For an example, the packaged image sensor 30 may be connected with a power supply or transmit image signals to a rear-end controller or a display device.

In one embodiment, the packaged image sensor 30 further comprises a pipe 36 and a second encapsulant 37. The pipe 36 is disposed inside the through-hole 314 and protrudes from the surface where the first electric-conduction contacts 311 are disposed. The second encapsulant 37 encapsulates the light-emitting element 33, the circuit board 35, one end of the plurality of conductive wires 353, and a portion of pipe 36. It is easily understood: the second encapsulant 37 is not allowed to cover or overflow to two openings at two ends of the pipe 36 so as to keep two ends of the pipe 36 opened. In one embodiment, the second encapsulant 37 includes a secondary optical structure 371. The secondary optical structure 371 is disposed on the light-output side of the light-emitting element 33. The secondary optical structure 371 can adjust the light-exiting angle so as to increase the utilization rate of illumination and the distance of illumination.

Based on the disclosed structure above, the pipe 36 may be positioned by the through-hole 314 of the substrate 31, whereby to maintain the relative position of the pipe 36 and the image sensor 32. In other words, the present invention does not need an additional design for fixing the position of the pipe 36; the present invention only needs to prevent the second encapsulant 37 from entering the pipe 36 while the second encapsulant 37 is filled. Therefore, the design of the mold chase is simpler in the present invention. Further, demolding is easy to be performed in the present invention.

Refer to FIG. 3 again. In one embodiment, the packaged image sensor 30 further comprises a plurality of steering control wires 38, which are connected with the substrate 31. The second encapsulant 37 encapsulates one end of the steering control wires 38 lest the steering control wires 38 be detached from the substrate 31. In the embodiment shown in FIG. 3, the steering control wires 38 are connected with the substrate 31. However, the present invention is not limited by the embodiment. For example, the steering control wires 38 may be connected with the circuit board 35. In one embodiment, the steering control wires 38 are connected with the substrate 31 via soldering, welding or snap-fitting, and the second encapsulant 37 is used to cover the position where the steering control wires 38 are connected lest the steering control line 38 be separated from the substrate 31.

The packaged image sensor 30 may be steered via pulling the steering control wires 38. In one embodiment, the pipe 36 and the second encapsulant 37 are made of flexible material. Based on the disclosed structure above, only the substrate 31 and the image sensor 32 are unbent along the optical axis. Thus, the bending radius of the packaged image sensor 30 of the present invention is significantly decreased. Therefore, the present invention can be applied to a situation needing a smaller bending radius.

Figure 4:
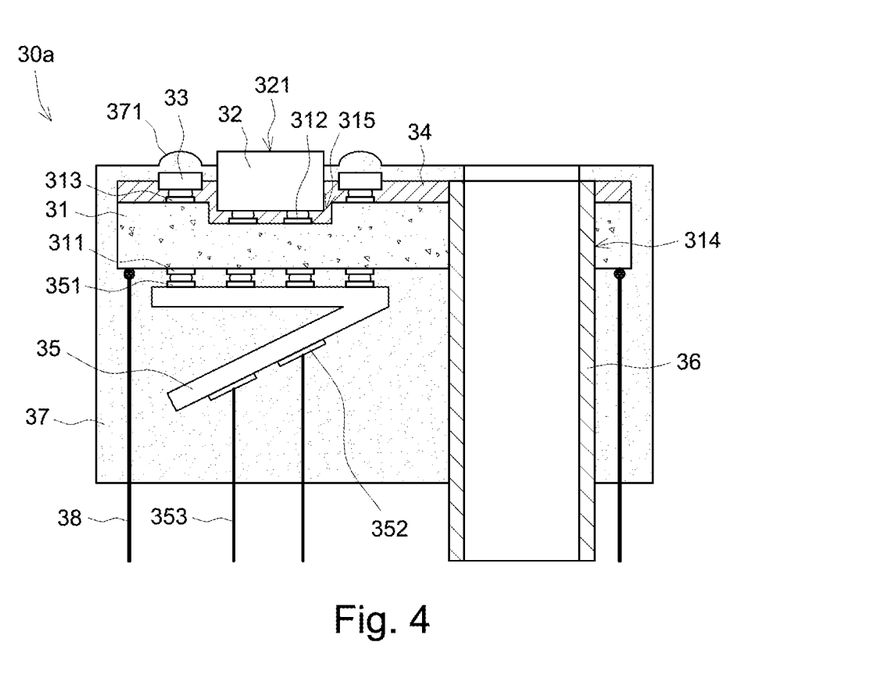
FIG. 4 is a diagram schematically showing a packaged image sensor according to a second embodiment of the present invention.

It should be explained herein: the relative altitude of the image sensor 32 and the light-emitting element 33 may influence the illumination and the imaging quality. For example, if the light-output surface 331 of the light-emitting element 33 is relatively too low with respect to the image sensor 32, the image sensor 32 may block the illuminating light emitted by the light-emitting element 33 and generate shadows; if the light-input surface 321 of the image sensor 32 is relatively too low with respect to the light-emitting element 33, the light-emitting element 33 may block the imaging light reflected by the inspected object; alternatively, the illuminating light emitted by the light-emitting element 33 may directly enter the image sensor 32 and affect the imaging quality. In one embodiment, the altitude of the light-input surface 321 of the image sensor 32 is equal to or higher than the altitude of the light-output surface 331 of the light-emitting element 33. It is preferred: the difference between the altitude of the light-input surface 321 of the image sensor 32 and the altitude of the light-output surface 331 of the light-emitting element 33 is equal to or smaller than 0.5 mm. Refer to FIG. 4. In one embodiment, the substrate 31 of the packaged image sensor 30a includes a recess 315; the plurality of second electric-conduction contacts 312 and the image sensor 32 are disposed on the bottom of the recess 315. Based on the abovementioned structure, the relative altitude of the light-input surface 321 of the image sensor 32 and the light-output surface 331 of the light-emitting element 33 may be controlled via adjusting the depth of the recess 315, whereby to optimize the illumination quality and the imaging quality.

Figure 5:
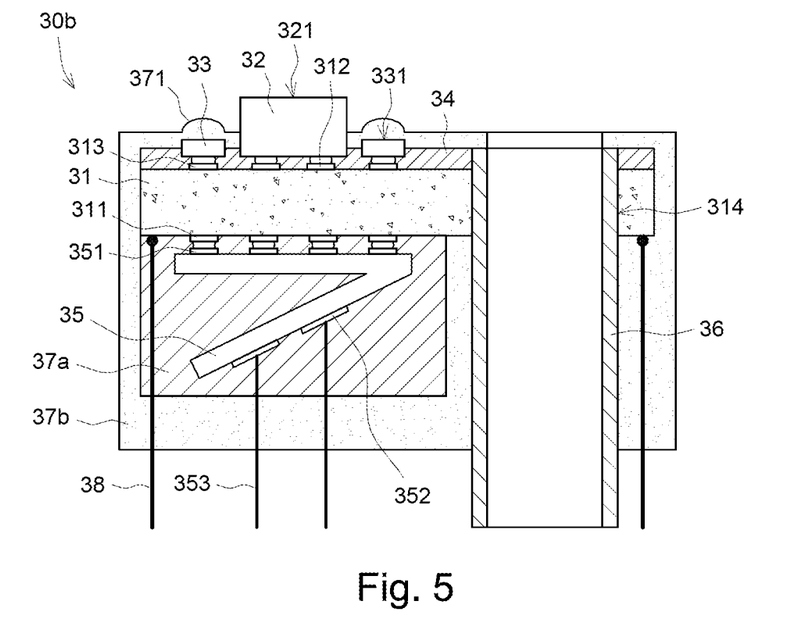
FIG. 5 is a diagram schematically showing a packaged image sensor according to a third embodiment of the present invention.
Figure 6:
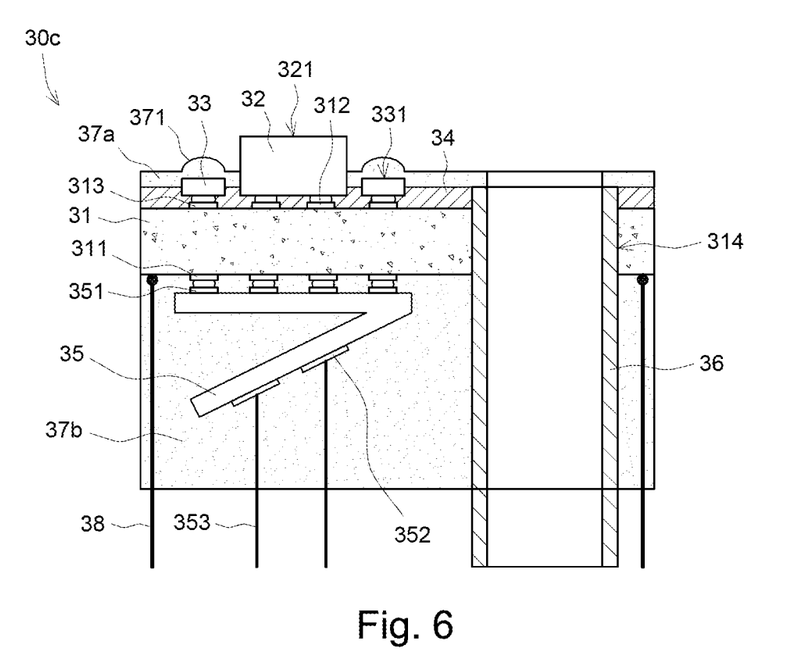
FIG. 6 is a diagram schematically showing a packaged image sensor according to a fourth embodiment of the present invention.

In the embodiments shown in FIG. 3 and FIG. 4, the encapsulation of the second encapsulant 37 is completed in a single operation. However, the present invention is not limited by these embodiments. Refer to FIG. 5. In one embodiment, the encapsulation of the second encapsulant of the packaged image sensor 30b is realized via several cycles of operations. For example, a second encapsulant 37a is used to encapsulate the circuit board 35 and the conductive wires 353 in a first cycle of operation; next, a second encapsulant 37b is used to encapsulate a portion of the pipe 36 and form second optical structures 371 in a second cycle of operation. Refer to FIG. 6. In the packaged image sensor 30c, the second encapsulant 37a is used to form the secondary optical structure 371 in the uncut substrate 31 beforehand; after cutting of the substrate 31, electric connection of the circuit board 35 and placement of the pipe 36, the second encapsulant 37b is used to realize the second cycle of encapsulation.

Figure 7A:
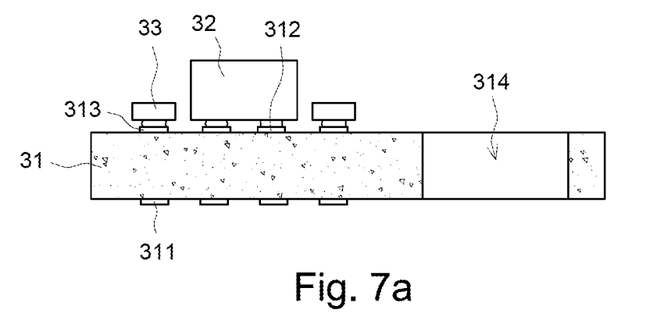
FIGS. 7a-7e are diagrams schematically showing a method for fabricating a packaged image sensor according to one embodiment of the present invention.

Refer to FIGS. 7a-7e for a method of fabricating the packaged image sensor 30 shown in FIG. 3. Refer to FIG. 7a. Firstly, provide a substrate 31. The substrate 31 includes a plurality of through-holes 314 arranged in array. The substrate 31 also includes a plurality of first electric-conduction contacts 311, a plurality of second electric-conduction contacts 312, and a plurality of third electric-conduction contacts 313, wherein the first electric-conduction contacts 311, the second electric-conduction contacts 312 and the third electric-conduction contacts 313 are corresponding to the through-holes 314. The image sensors 32 are joined with the substrate 31 in a bonding method and electrically connected with the corresponding second electric-conduction contacts 312. The light-emitting elements 33 are also disposed on the substrate 31 and electrically connected with the corresponding third electric-conduction contacts 313.

Figure 7B:
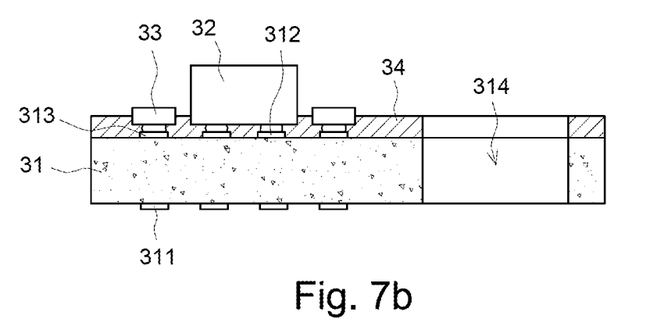

Refer to FIG. 7b. Next, fill the first encapsulant 34 into a space between the image sensors 32 and the light-emitting elements 33, and cure the first encapsulant 34 in an ultraviolet method, a thermal method or another appropriate method. It is easily understood: after the first encapsulant 34 is cured, the through-holes 314 of the substrate 31 should be kept opened. Next, cut the substrate along the cutting alignment marks or the cutting lines to generate image sensor modules each including the image sensor 32 and the light-emitting elements 33.

Figure 7C:
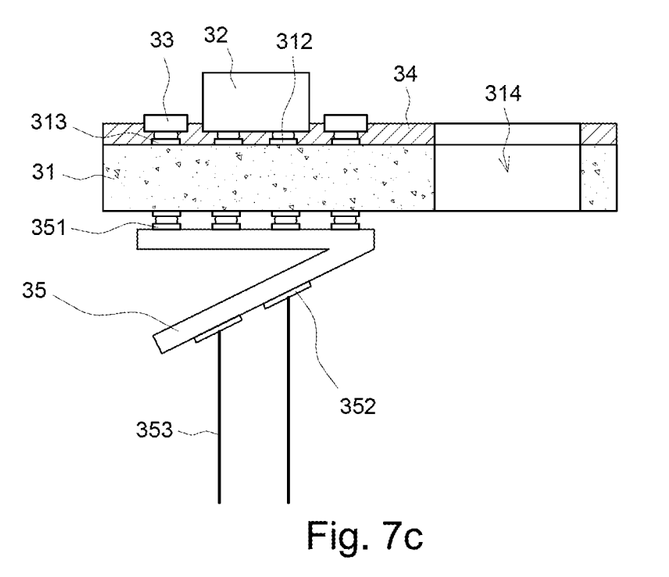

Refer to FIG. 7c. Next, dispose the separated image sensor module on the circuit board 35 in a surface mount technology (SMT) or another appropriate technology, and electrically connect the image sensor module with the circuit board 35. Next, electrically connect a plurality of conductive wires 353 with the corresponding fifth electric-conduction contacts 352 of the circuit board 35.

Figure 7D:
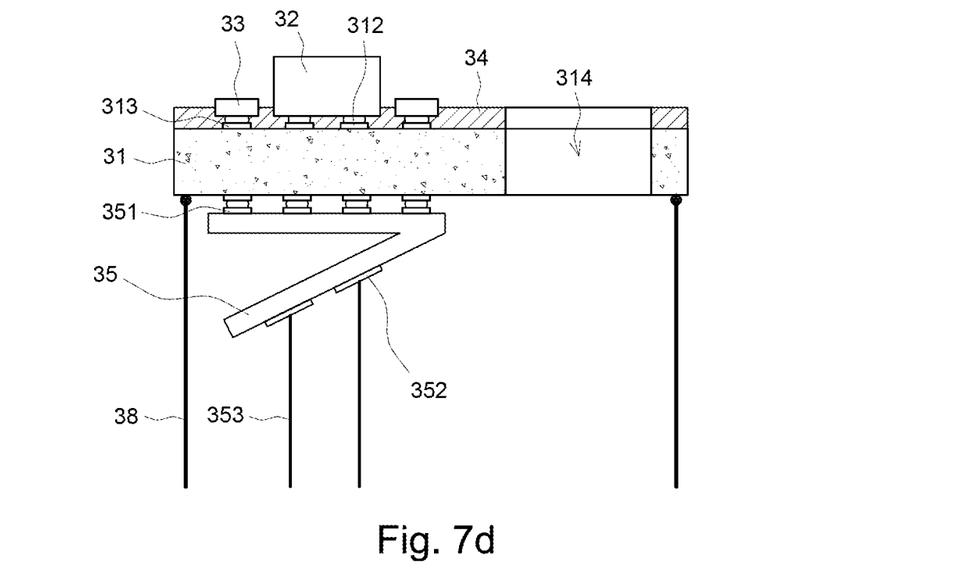
Figure 7E:
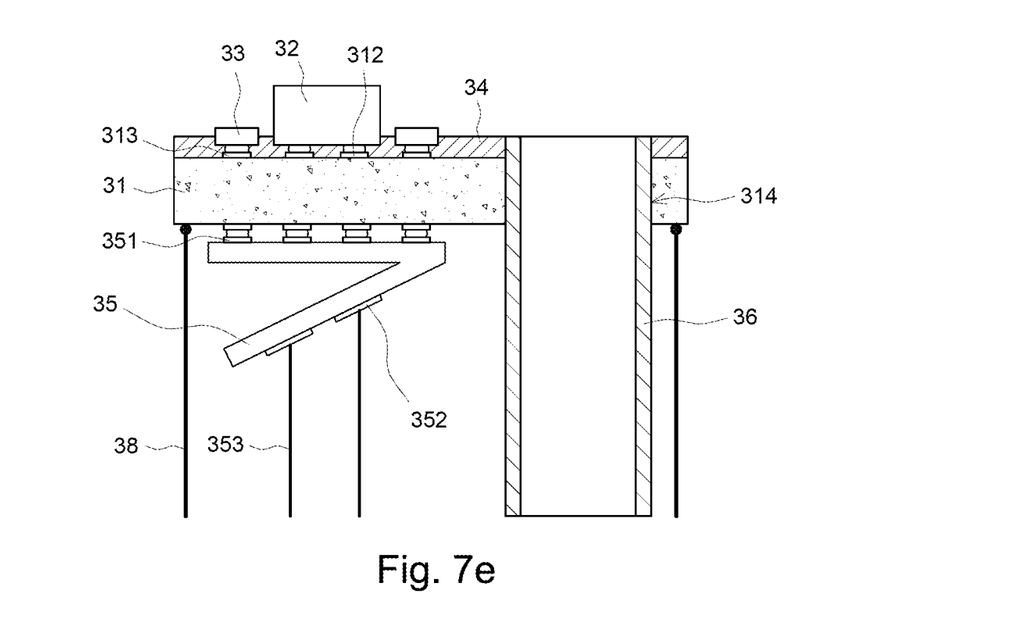

Refer to FIG. 7d. Next, join the steering control wires 38 to the substrate 31. Refer to FIG. 7e. Next, place the pipe 36 inside the through-hole 314 of the substrate 31 and secure the pipe 36 roughly. It should be explained herein: the step of FIG. 7d and the step of FIG. 7e may be exchanged in their orders or undertaken simultaneously. Then, place the module shown in FIG. 7e in a mold chase, and fill the second encapsulant 37 into the mold chase for package, wherein the secondary optical structure 371 is formed on the light-output side of the light-emitting element 33. The packaged image sensor 30 is completed shown in FIG. 3.

Figure 8:
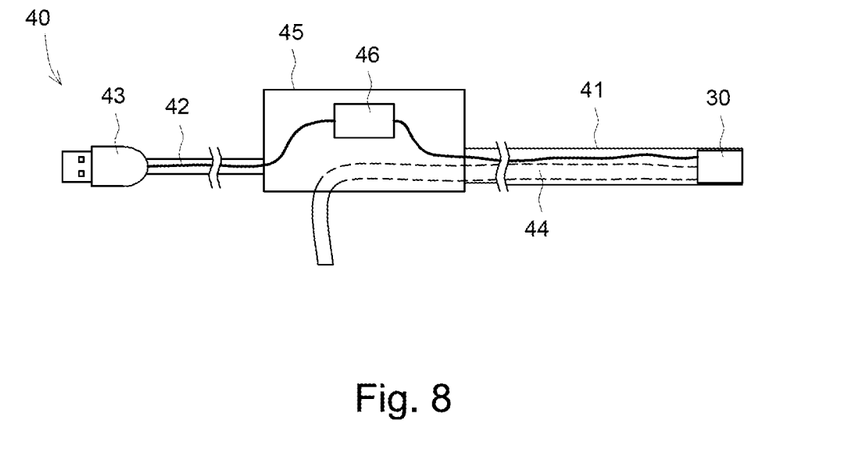
FIG. 8 is a diagram schematically showing an endoscope according to one embodiment of the present invention.

Refer to FIG. 8. In one embodiment, the endoscope 40 of the present invention comprises a tube 41, a packaged image sensor 30, a plurality of conductive wires 42, an electric connector 43 and a working channel 44. The tube 41 includes a first opening and a second opening. The end of the first opening of the tube 41 of the endoscope 40 is extended to a cavity, such as a cavity of a human body or a small space to be inspected in an industrial inspection. It is easily understood: the tube 41 may be designed to have different appearances to meet different applications. The packaged image sensor 30 is disposed at the first opening of the tube 41, whereby to capture images of a cavity and generate corresponding signals. The detailed structure of the packaged image sensor 30 has been described hereinbefore and will not repeat again. The working channel 44 may extend from the pipe 36 of the packaged image sensor 30 shown in FIG. 3. Alternatively, the working channel 44 is another pipe connected with the pipe 36 of the packaged image sensor 30. The operator may extend a working instrument through the working channel 44 into a cavity to undertake an intended work, such as sampling tissue, sucking out secretions/tissue fluids/blood, or supplying medicine.

The conductive wires 42 are respectively electrically connected with the packaged image sensor 30 and the electric connector 43, whereby the electronic signals generated by the packaged image sensor 30 may be transmitted to an external electronic device, such as a computer, a mobile Internet-access device or a dedicated electronic device of the endoscope, through the electric connector 43. In one embodiment, the electric connector 43 is electrically connected with an external electronic device in a pluggable way. The electric connector 43 may be a USB interface, a connection interface of a mobile Internet-access device or another appropriate electric connector.

In one embodiment, the endoscope 40 of the present invention further comprises a housing 45. The housing 45 is disposed between the tube 41 and the electric connector 43. The design of the housing 45 may be varied according to requirement. For an example, the housing 45 may have an appearance suitable to be held by the operator. For another example, the shape of the housing 45 is suitable to be mounted on a carrier, such as a head-mounted carrier. In one embodiment, the endoscope 40 of the present invention further comprises an electronic element 46. The electronic element 46 is electrically connected with the packaged image sensor 30 and the electric connector 43. The electronic element 46 can process the electronic signals generated by the packaged image sensor 30 and transmit the electronic signals to an external electronic device through the electric connector 43. In one embodiment, the electronic element 46 is a microcontroller unit (MCU).

In conclusion, the present invention proposes a packaged image sensor and an endoscope using the same, wherein the image sensor and the light-emitting element are disposed on a substrate, and the through-hole of the substrate is used to define the relative position of the pipe and the image sensor. In the packaging process, the relative position of the pipe and the image sensor will be secured via merely placing the pipe inside the through-hole, and demolding is easy to perform after the encapsulant is cured. Besides, the steering control wires are joined to the substrate or the circuit; the pipe and the encapsulant are made of flexible material. Therefore, the packaged image sensor and the endoscope using the same may have a smaller bending radius and thus may apply to a narrower space where a smaller bending radius is required.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the appended claims.

What is claimed is:

1. A packaged image sensor, comprising:
a substrate, including a first surface, a second surface opposite to the first surface, a through-hole, a plurality of first electric-conduction contacts, a plurality of second electric-conduction contacts, and a plurality of third electric-conduction contacts, wherein the plurality of second electric-conduction contacts and the plurality of third electric-conduction contacts are disposed on the first surface, the plurality of first electric-conduction contacts are disposed on the second surface, and the plurality of second electric-conduction contacts and the plurality of third electric-conduction contacts are electrically connected with the plurality of corresponding first electric-conduction contacts;
an image sensor, disposed on the substrate and electrically connected with the plurality of second electric-conduction contacts;
a light-emitting element, disposed on the substrate and near the image sensor and electrically connected with the plurality of third electric-conduction contacts; and
a first encapsulant, filled into a space between the image sensor and the light-emitting element with the through-hole of the substrate kept opened;
wherein a pipe is disposed inside the through-hole of the substrate and protruding from the second surface of the substrate where the first electric-conduction contacts are disposed.

2. The packaged image sensor according to claim 1, further comprising:
a secondary optical structure, disposed on a light-output side of the light-emitting element.

3. The packaged image sensor according to claim 1, further comprising:
a circuit board, including a third surface, a fourth surface different from the third surface, a plurality of fourth electric-conduction contacts and a plurality of fifth electric-conduction contacts, wherein the plurality of fourth electric-conduction contacts are disposed on the third surface, the plurality of fifth electric-conduction contacts are disposed on the fourth surface, the plurality of fourth electric-conduction contacts are electrically connected with the plurality of corresponding first electric-conduction contacts of the substrate; and
a plurality of conductive wires, electrically connected with the plurality of corresponding fifth electric-conduction contacts.

4. The packaged image sensor according to claim 3, further comprising:
a second encapsulant, encapsulating the circuit board and one end of the plurality of conductive wires.

5. The packaged image sensor according to claim 3, further comprising:
a pipe, disposed inside the through-hole of the substrate and protruding from a surface of the substrate where the first electric-conduction contacts are disposed; and
a second encapsulant, encapsulating the light-emitting element, the circuit board, one end of the plurality of conductive wires, and a portion of the pipe, and keeping two ends of the pipe opened.

6. The packaged image sensor according to claim 5, wherein the second encapsulant includes a secondary optical structure, which is disposed corresponding to the light-emitting element.

7. The packaged image sensor according to claim 5, further comprising:
a plurality of steering control wires, which is connected with the substrate or the circuit board, wherein the second encapsulant encapsulates one end of the steering control wires.

8. The packaged image sensor according to claim 7, wherein the second encapsulant is made of a flexible material.

9. The packaged image sensor according to claim 1, wherein the substrate includes a recess; the plurality of second electric-conduction contacts and the image sensor are disposed on a bottom of the recess.

10. The packaged image sensor according to claim 1, wherein an altitude of a light-input surface of the image sensor is equal to or higher than an altitude of a light-output surface of the light-emitting element.

11. The packaged image sensor according to claim 1, wherein the packaged image sensor comprises a plurality of light-emitting elements; the plurality of light-emitting elements emits light beams having an identical wavelength or respectively emits light beams having different wavelengths or spectrums.

12. The packaged image sensor according to claim 1, wherein the first encapsulant is made of a semi-transparent resin or an opaque resin.

\* \* \* \* \*